United States Patent
Ogata

(10) Patent No.: US 10,928,628 B2
(45) Date of Patent: Feb. 23, 2021

(54) OPTICAL FIBER SCANNING APPARATUS AND ENDOSCOPE

(71) Applicant: OLYMPUS CORPORATION, Tokyo (JP)

(72) Inventor: Masanori Ogata, Matsumoto (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/449,866

(22) Filed: Jun. 24, 2019

(65) Prior Publication Data

US 2019/0310466 A1 Oct. 10, 2019

Related U.S. Application Data

(63) Continuation of application No. PCT/JP2016/088693, filed on Dec. 26, 2016.

(51) Int. Cl.
| | |
|---|---|
| *G02B 6/00* | (2006.01) |
| *A61B 1/07* | (2006.01) |
| *G02B 26/10* | (2006.01) |
| *F21V 8/00* | (2006.01) |

(Continued)

(52) U.S. Cl.
CPC .............. *G02B 26/103* (2013.01); *A61B 1/07* (2013.01); *G02B 6/0006* (2013.01); *G02B 6/0008* (2013.01); *G02B 23/2469* (2013.01); *G02B 26/10* (2013.01); *H04N 5/2256* (2013.01); *H04N 2005/2255* (2013.01)

(58) Field of Classification Search
CPC ............ G02B 26/103; G02B 6/00; A61B 1/07

USPC ......................................................... 385/117
See application file for complete search history.

(56) References Cited

U.S. PATENT DOCUMENTS

| | | | | |
|---|---|---|---|---|
| 5,115,814 | A | * | 5/1992 | Griffith .................... A61B 5/06 600/439 |
| 5,176,140 | A | * | 1/1993 | Kami ...................... A61B 8/12 310/327 |

(Continued)

FOREIGN PATENT DOCUMENTS

| | | | |
|---|---|---|---|
| JP | 2008-116922 A | 5/2008 | |
| JP | 2008116922 A | * 5/2008 | ......... G02B 23/2407 |

(Continued)

OTHER PUBLICATIONS

International Search Report dated Feb. 14, 2017 received in PCT/JP2016/088693.

*Primary Examiner* — Kaveh C Kianni

(74) *Attorney, Agent, or Firm* — Scully, Scott, Murphy & Presser, P.C.

(57) ABSTRACT

An optical fiber scanning apparatus includes an optical fiber a fixed end of which is fixed and a free end for emitting illumination light of which vibrates in a first direction and a second direction, a ferrule which includes a through hole including an opening on a distal end surface and fixes the optical fiber inserted through the through hole, a pair of first fixing members which sandwich and fix the optical fiber in the first direction, a pair of second fixing members which sandwich and fix the optical fiber in the second direction, and piezoelectric elements or a magnet configured to vibrate the optical fiber, in which a Young's modulus of the pair of first fixing members is smaller than a Young's modulus of the pair of second fixing members.

6 Claims, 6 Drawing Sheets

(51) Int. Cl.
*G02B 23/24* (2006.01)
*H04N 5/225* (2006.01)

(56) References Cited

U.S. PATENT DOCUMENTS

| | | | | |
|---|---|---|---|---|
| 5,682,412 A * | 10/1997 | Skillicorn | ............... | A61B 6/06 378/113 |
| 5,838,000 A * | 11/1998 | Mertesdorf | ............ | B82Y 20/00 250/234 |
| 6,294,775 B1 | 9/2001 | Seilbel et al. | | |
| 6,419,401 B1 * | 7/2002 | Taira | ...................... | G02B 6/381 385/55 |
| 6,687,010 B1 * | 2/2004 | Horii | ................... | G01B 9/0201 356/479 |
| 6,845,190 B1 * | 1/2005 | Smithwick | ........... | A61B 1/0008 385/1 |
| 7,129,472 B1 * | 10/2006 | Okawa | ................ | A61B 1/00059 250/234 |
| 2001/0007917 A1 * | 7/2001 | Hayakawa | ............ | B29C 48/34 600/139 |
| 2002/0126961 A1 * | 9/2002 | Hirabayashi | ......... | G02B 6/3834 385/78 |
| 2002/0146215 A1 * | 10/2002 | Ogawa | ................. | G02B 6/3882 385/80 |
| 2003/0020922 A1 * | 1/2003 | Crowley | ............. | G01B 9/02028 356/502 |
| 2004/0151466 A1 * | 8/2004 | Crossman-Bosworth | .................... | G02B 6/25 385/140 |
| 2004/0156124 A1 * | 8/2004 | Okada | .................. | G02B 27/021 359/754 |
| 2004/0158129 A1 * | 8/2004 | Okada | ..................... | A61B 1/05 600/168 |
| 2004/0181148 A1 * | 9/2004 | Uchiyama | ............ | G01N 21/474 600/425 |
| 2004/0254474 A1 * | 12/2004 | Seibel | ................... | A61B 5/0066 600/473 |
| 2005/0213892 A1 * | 9/2005 | Barnes | ................. | G02B 6/3806 385/62 |
| 2006/0013528 A1 * | 1/2006 | Rosman | ............... | G02B 26/101 385/25 |
| 2006/0132791 A1 * | 6/2006 | Toida | ................... | A61B 5/0066 356/479 |
| 2006/0170930 A1 * | 8/2006 | Li | ...................... | G01B 9/02091 356/479 |
| 2006/0241493 A1 * | 10/2006 | Feldman | ............... | A61B 8/4461 600/476 |
| 2006/0244973 A1 * | 11/2006 | Yun | .................... | G01B 9/02091 356/511 |
| 2006/0255250 A1 * | 11/2006 | Chong | ............... | G02B 26/0858 250/227.11 |
| 2007/0016062 A1 * | 1/2007 | Park | ......................... | A61B 8/12 600/459 |
| 2007/0019906 A1 * | 1/2007 | Melville | ................. | G02B 6/262 385/25 |
| 2007/0078305 A1 * | 4/2007 | Teramura | ........... | G02B 23/2469 600/139 |
| 2007/0115477 A1 * | 5/2007 | Teramura | ............ | G01N 21/4795 356/479 |
| 2007/0232902 A1 * | 10/2007 | Teramura | ............ | A61B 5/6852 600/425 |
| 2007/0239032 A1 * | 10/2007 | Milner | ............... | A61B 5/6852 600/476 |
| 2007/0244357 A1 * | 10/2007 | Wiklof | .............. | A61B 1/00165 600/109 |
| 2007/0244365 A1 * | 10/2007 | Wiklof | .............. | A61B 1/00096 600/173 |
| 2007/0287920 A1 * | 12/2007 | Sawada | ............. | A61B 8/4488 600/463 |
| 2008/0004491 A1 * | 1/2008 | Karasawa | ............ | G02B 6/241 600/101 |
| 2008/0039693 A1 * | 2/2008 | Karasawa | ........... | A61B 1/00165 600/175 |
| 2008/0058629 A1 * | 3/2008 | Seibel | ................ | A61B 1/00172 600/368 |
| 2008/0073517 A1 * | 3/2008 | Melville | ................ | G02B 7/008 250/306 |
| 2008/0078939 A1 * | 4/2008 | Hennessy | ............... | G03B 42/04 250/370.09 |
| 2008/0161648 A1 * | 7/2008 | Karasawa | ........... | A61B 1/0017 600/182 |
| 2008/0165360 A1 * | 7/2008 | Johnston | ................ | G06T 7/80 356/394 |
| 2008/0221388 A1 * | 9/2008 | Seibel | ............. | A61B 1/00177 600/109 |
| 2008/0243031 A1 * | 10/2008 | Seibel | ................. | A61B 10/02 600/566 |
| 2008/0249369 A1 * | 10/2008 | Seibel | .................. | G02B 23/26 600/182 |
| 2009/0024191 A1 * | 1/2009 | Seibel | ............... | A61B 1/00172 607/92 |
| 2009/0026888 A1 * | 1/2009 | Melville | ............. | A61B 1/00172 310/335 |
| 2009/0028407 A1 * | 1/2009 | Seibel | ................ | A61B 1/0008 382/131 |
| 2009/0208143 A1 * | 8/2009 | Yoon | ...................... | A61B 5/065 382/321 |
| 2009/0244260 A1 * | 10/2009 | Takahashi | ............ | A61B 5/1076 348/45 |
| 2009/0316116 A1 * | 12/2009 | Melville | .................. | A61B 1/07 353/31 |
| 2011/0235049 A1 * | 9/2011 | Burnett | ..................... | G01J 9/04 356/484 |
| 2013/0345508 A1 * | 12/2013 | Akui | ................. | A61B 1/00172 600/109 |
| 2014/0073950 A1 * | 3/2014 | Akui | .................. | A61B 1/07 600/478 |
| 2014/0194691 A1 * | 7/2014 | Imaizumi | ................. | A61B 1/07 600/178 |
| 2014/0232993 A1 | 8/2014 | Kim | | |
| 2014/0236022 A1 * | 8/2014 | Zeng | ................... | A61B 1/0125 600/476 |
| 2014/0286604 A1 * | 9/2014 | Gweon | ................ | G02B 26/103 385/13 |
| 2014/0323878 A1 * | 10/2014 | Toriumi | ................. | G02B 21/0076 600/478 |
| 2015/0005579 A1 * | 1/2015 | Yamabe | ............ | A61B 1/00057 600/109 |
| 2015/0029570 A1 * | 1/2015 | Ito | .......................... | G02B 23/24 359/198.1 |
| 2015/0080718 A1 * | 3/2015 | Wheatley | ........... | A61B 1/00071 600/429 |
| 2015/0173603 A1 * | 6/2015 | Wheatley | ............. | G01B 9/0205 600/425 |
| 2015/0173604 A1 * | 6/2015 | Wheatley | ............. | G02B 26/103 600/425 |
| 2015/0320307 A1 * | 11/2015 | Wheatley | ............... | A61B 3/102 351/206 |
| 2015/0327760 A1 * | 11/2015 | Wheatley | ............... | A61B 3/102 351/206 |
| 2016/0356965 A1 * | 12/2016 | Watanabe | ........... | G02B 6/3861 |
| 2017/0176742 A1 * | 6/2017 | Kasai | .................... | G02B 23/26 |
| 2017/0238792 A1 * | 8/2017 | Yokota | ..................... | A61B 1/07 |
| 2017/0248784 A1 * | 8/2017 | Fujiwara | ............. | G02B 26/103 |
| 2020/0025665 A1 * | 1/2020 | Trainer | ............... | G01N 15/0205 |

FOREIGN PATENT DOCUMENTS

| | | | |
|---|---|---|---|
| JP | 2012-078389 A | 4/2012 | |
| JP | 2014-044265 A | 3/2014 | |
| JP | 2014044265 A | * 3/2014 | ......... A61B 1/00165 |
| JP | 2015-232493 A | 12/2015 | |
| WO | 2015/190498 A1 | 12/2015 | |

* cited by examiner

OPTICAL FIBER SCANNING APPARATUS AND ENDOSCOPE

CROSS REFERENCE TO RELATED APPLICATION

This application is a continuation application of PCT/JP2016/088693 filed on Dec. 26, 2016, the entire contents of which are incorporated herein by this reference.

BACKGROUND OF INVENTION

1. Field of the Invention

The present invention relates to an optical fiber scanning apparatus including an optical fiber a free end of which vibrates in a first direction and a second direction perpendicular to the first direction, and an endoscope including the optical fiber scanning apparatus in a distal end portion of an insertion section.

2. Description of the Related Art

An image pickup apparatus including an image pickup device such as a CCD or a CMOS image sensor simultaneously receives reflected light from a subject using many light receiving elements arranged in a matrix shape, to acquire an object image. In an endoscope which shoots a dark inside of a body, an image in a range illuminated with light from a light source is acquired.

On the other hand, an optical scanning type image pickup apparatus sequentially receives, while scan-irradiating an object with a light spot, reflected light from the object, to generate an object image based on data representing the received light.

For example, the optical scanning type image pickup apparatus performs the scanning irradiation with the light spot when an optical fiber scanning apparatus vibrates a free end of an optical fiber in a cantilevered state which guides light from a light source to perform two-dimensional scanning.

Examples of means for vibrating the optical fiber include a piezoelectric driving method for attaching a piezoelectric element to an optical fiber and vibrating the piezoelectric element disclosed in U.S. Pat. No. 6,294,775 and an electromagnetic driving method for vibrating a permanent magnet attached to an optical fiber using an electromagnetic coil disclosed in Japanese Patent Application Laid-Open Publication No. 2008-116922. If the optical fiber is vibrated, when the optical fiber is vibrated in the vicinity of a resonance frequency of the optical fiber, a large deflection (displacement or amplitude) of the optical fiber is obtained with small energy.

To cause the free end of the optical fiber to scan two-dimensionally, X-axis direction scanning and Y-axis direction scanning, perpendicular to the X-axis direction need to be independently controlled. However, if both the scannings have the same resonance frequency, even when the free end of the optical fiber is scanning in the X-axis direction, for example, the free end of the optical fiber also unintentionally scans in the Y-axis direction. Thus, a distortion may occur in a scan trajectory.

Japanese Patent Application Laid-Open Publication No. 2014-44265 discloses an optical scanning apparatus which includes an optical fiber having different resonance frequencies, respectively, in an X-axis direction and a Y-axis direction and performs stable scanning irradiation.

SUMMARY OF THE INVENTION

An optical fiber scanning apparatus according to an aspect of the present invention includes an optical fiber a fixed end of which is fixed and a free end for emitting illumination light of which vibrates in a first direction and a second direction perpendicular to the first direction, a ferrule which includes a through hole including an opening on a distal end surface and fixes the fixed end of the optical fiber inserted through the through hole, a pair of first fixing members which sandwich and fix the optical fiber in the first direction, a pair of second fixing members which sandwich and fix the optical fiber in the second direction, and piezoelectric elements or a magnet configured to vibrate the optical fiber, in which a Young's modulus of the pair of first fixing members is smaller than a Young's modulus of the pair of second fixing members.

An endoscope according to another aspect of the invention includes an optical fiber scanning apparatus in a distal end portion of an insertion section, the optical fiber scanning apparatus including an optical fiber a fixed end of which is fixed and a free end for emitting illumination light of which vibrates in a first direction and a second direction perpendicular to the first direction, a ferrule which includes a through hole including an opening on a distal end surface and fixes the fixed end of the optical fiber inserted through the through hole, a pair of first fixing members which sandwich and fix the optical fiber in the first direction, a pair of second fixing members which sandwich and fix the optical fiber in the second direction, and piezoelectric elements or a magnet configured to vibrate the optical fiber, in which a Young's modulus of the pair of first fixing members is smaller than a Young's modulus of the pair of second fixing members.

DETAILED DESCRIPTION OF THE PREFERRED EMBODIMENTS

First Embodiment

An embodiment of the present invention will be described below with reference to the drawings.

Figure 1:
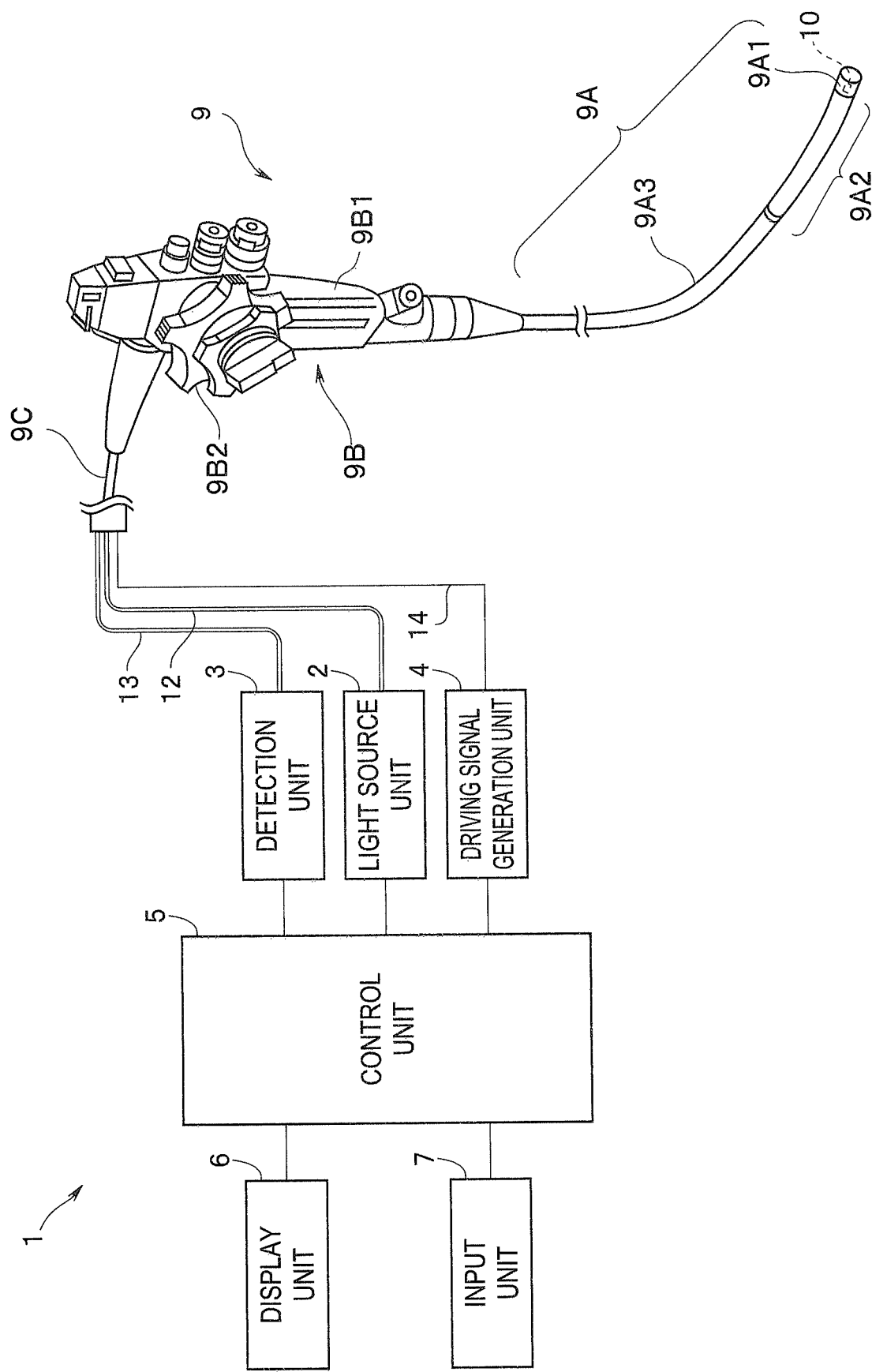
FIG. 1 is a configuration diagram of an endoscope system including an optical fiber endoscope according to a first embodiment.

As illustrated in FIG. 1, an endoscope 9 including an optical fiber scanning apparatus 10, together with a light source unit 2, a detection unit 3, a driving signal generation unit 4, a control unit 5, a display unit 6, and an input unit 7, constitutes an endoscope system 1.

Note that in the following description, it should be noted that the drawings based on each of embodiments are schematic, and a relationship between a thickness and a width of each of sections, a ratio of thicknesses of the sections, and the like respectively differ from actual ones, and the sections which also differ in a dimensional relationship and a ratio among the drawings may be included. Illustration of some of components and assignment of reference numerals may be omitted.

The endoscope 9 includes an elongated insertion section 9A to be inserted into a living body, an operation section 9B, and a universal cable 9C. The insertion section 9A in the endoscope 9 includes a distal end portion 9A1, a bending portion 9A2, and a flexible tube portion 9A3. Note that the endoscope 9 according to the embodiment is a so-called flexible endoscope, but the endoscope 9 may be a so-called rigid endoscope in which the insertion section 9A is rigid and may be used for medical and industrial purposes.

In the operation section 9B, a bending operation knob 9B2 for performing a bending operation for the bending portion 9A2 is turnably disposed. A connection section between the insertion section 9A and the operation section 9B is a grasping section 9B1 to be grasped by a user.

Figure 2:
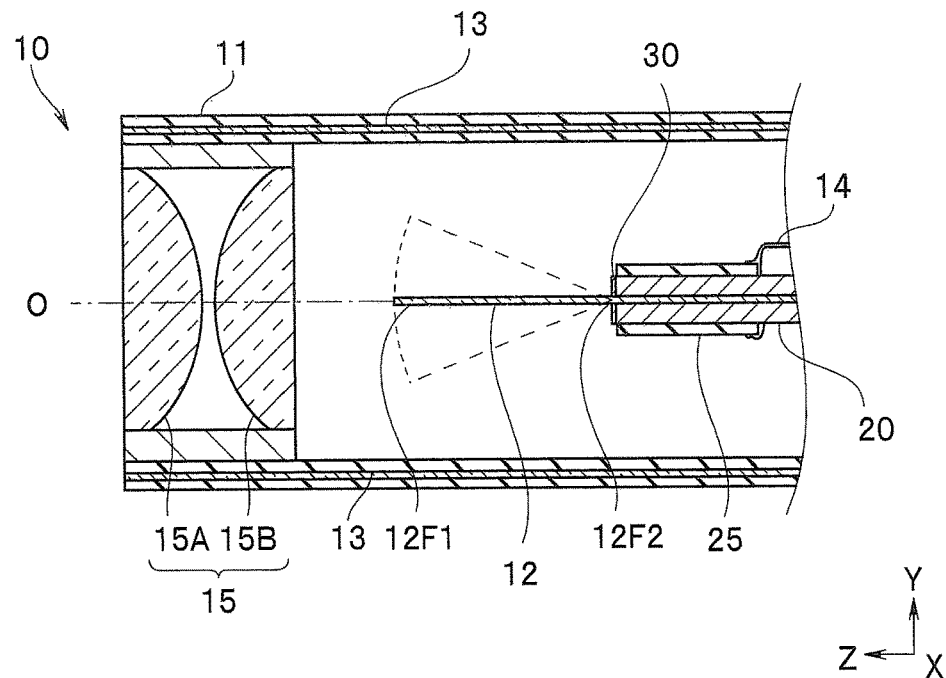
FIG. 2 is a cross-sectional view of an optical fiber scanning apparatus according to the first embodiment.
Figure 3:
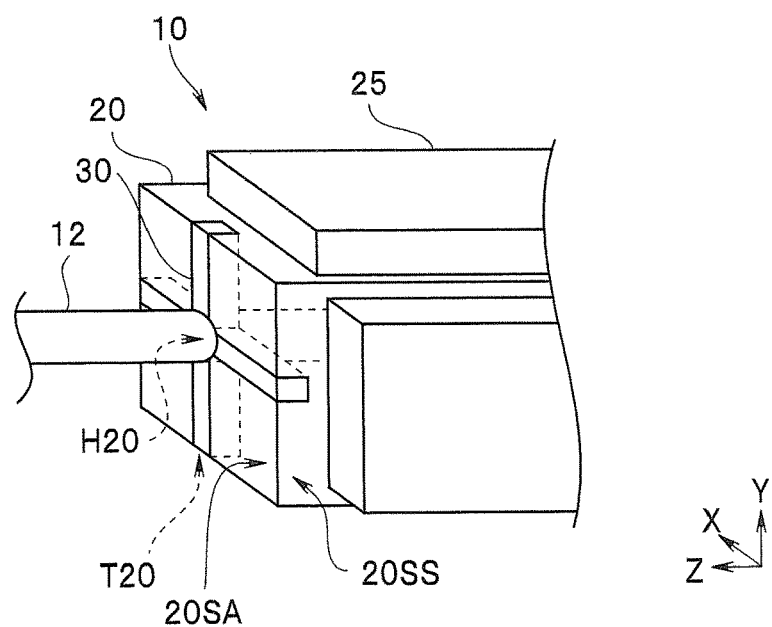
FIG. 3 is a perspective view of a principal part of the optical fiber scanning apparatus according to the first embodiment.
Figure 4:
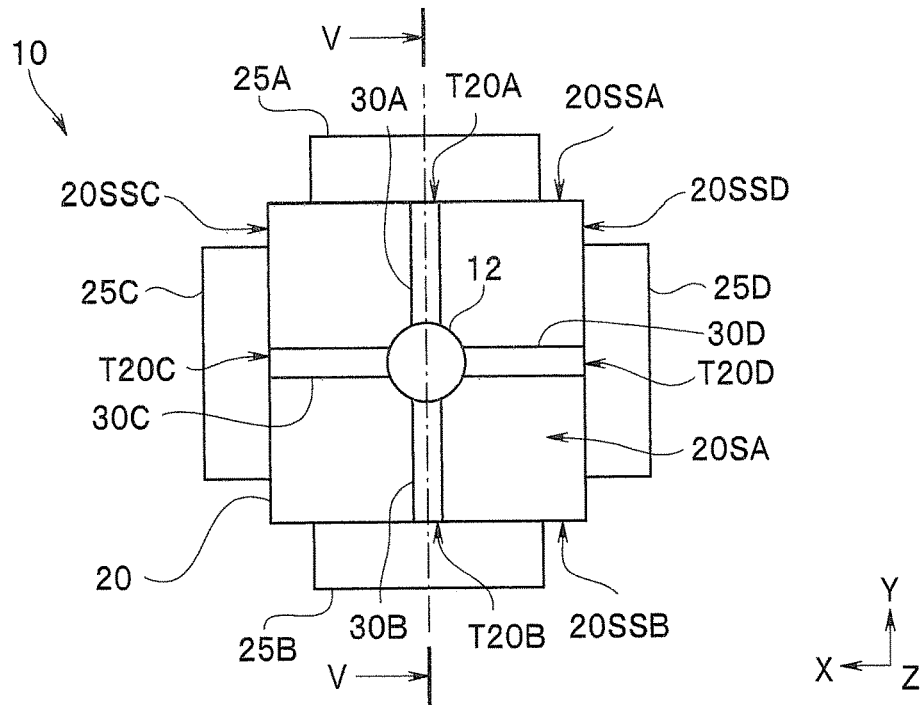
FIG. 4 is a front view of the principal part of the optical fiber scanning apparatus according to the first embodiment.
Figure 5:
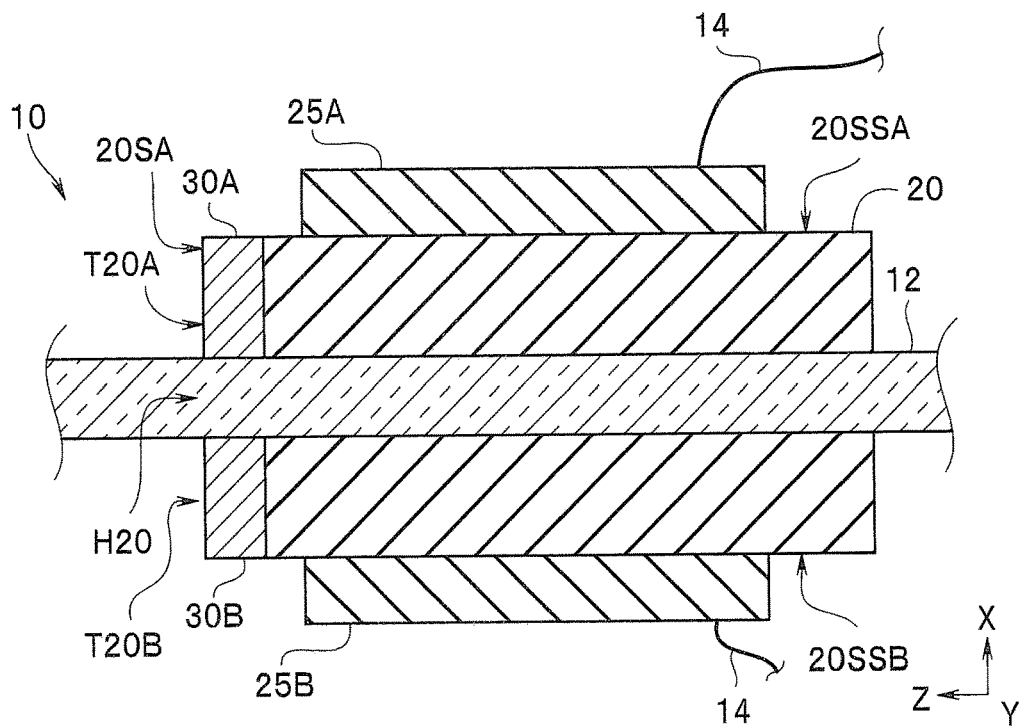
FIG. 5 is a cross-sectional view along a V-V line illustrated in FIG. 4 of the principal part of the optical fiber scanning apparatus according to the first embodiment.

An optical fiber 12 for illumination, an optical fiber 13 for light receiving, a signal line 14 configured to transmit a driving signal from the driving signal generation unit 4 to a driving section 25 (see FIG. 2) including piezoelectric elements, and the like are inserted through the universal cable 9C and the insertion section 9A and are connected to the optical fiber scanning apparatus 10 disposed in the distal end portion 9A1.

The light source unit 2 multiplexes respective light beams from three laser light sources each configured to emit CW (consecutive oscillation) laser light in three primary colors, e.g., red, green, and blue, and emits the multiplexed light beams as white light. Examples of the laser light source which can be used include a DPSS (diode pumped solid state) laser and a laser diode. Needless to say, a configuration of the light source unit 2 is not limited to this. Examples of the light source unit 2 may include a light source unit using one laser light source and a light source unit using other plurality of light sources.

When a distal end portion as a cantilever of the optical fiber 12 vibrates by the driving section 25, spot illumination light to be emitted by the optical fiber 12 is caused to scan two-dimensionally to illuminate an object to be observed, as described below. Reflected light from the object to be observed illuminated with the illumination light enters the detection unit 3 via the optical fiber 13 for detection. The detection unit 3 decomposes the reflected light into spectral components, and converts the spectral components into an electric signal using a photodiode. The control unit 5 synchronously controls the light source unit 2, the detection unit 3, and the driving signal generation unit 4 while processing the electric signal to be outputted by the detection unit 3, to synthesize images and display a composite image on the display unit 6. The user performs settings of the endoscope system 1, such as a scanning speed and brightness of the displayed image, via the input unit 7.

Note that the light source unit 2, the detection unit 3, the driving signal generation unit 4, and the control unit 5 may be accommodated in the same housing, or may be respectively accommodated in different housings.

As illustrated in FIGS. 2 to 5, the optical fiber scanning apparatus 10 includes a housing 11, optical fibers 12 and 13, a ferrule 20 as a holding section, the driving section 25 configured to vibrate the optical fiber 12, and an illumination optical system 15.

The optical fiber 12 guides the light from the light source unit 2, and emits illumination light from a free end 12F1. The illumination optical system 15 including a plurality of lenses 15A and 15B is configured to converge the spot illumination light emitted from the optical fiber 12 on a surface of the object to be observed. Note that the illumination optical system 15 is not limited to a two-element lens, but may include one lens or three or more lenses.

The optical fiber 13 for detection may have a light-converging optical system disposed at the distal end of the optical fiber 13. Note that the optical fiber scanning apparatus 10 includes a plurality of optical fibers 13 to obtain a sufficient amount of detected light.

The ferrule 20 composed of zirconia, for example, includes a through hole H20 having an opening on a distal end surface 20SA. A material for the ferrule 20 is not limited to ceramic such as zirconia if a rigid material. The ferrule 20 may be composed of metal such as nickel or resin. An inner diameter of the through hole H20 is slightly larger than an outer diameter of the optical fiber 12. For example, the inner diameter of the through hole H20 is larger than 100% and not more than 105% of the outer diameter of the optical fiber 12. A distal end portion of the optical fiber 12 inserted into the through hole H20 constitutes a cantilever to which a fixed end 12F2 is fixed and which is held along a central axis (optical axis) O in a long-axis direction (Z-axis direction) of the housing 11.

The optical fiber 12 is a vibration section constituting a cantilever in which a distal end portion in a range from the fixed end 12F2 as a starting point to the free end 12F1 vibrates in a first direction (Y-axis direction) and a second direction (X-axis direction) perpendicular to the first direction. The first direction and the second direction are perpendicular to the optical axis direction (Z-axis direction). Note that it goes without saying that the first direction may be the X-axis direction and the second direction may be the Y-axis direction.

The free end 12F1 of the optical fiber 12 moves in a predetermined scanning pattern within an XY plane by a combination of the vibration in the first direction and the vibration in the second direction.

Examples of a scanning method include spiral scanning, raster scanning, and Lissajous scanning depending on a combination of a vibration pattern in the first direction (Y-axis scanning) and a vibration pattern in the second direction (X-axis scanning).

The spiral scanning is performed while spirally changing a diameter by continuously changing a displacement amount in the first direction and a displacement amount in the second direction. The raster scanning is performed by combining low-speed scanning in the first direction and high-speed scanning in the second direction performed during the scanning in the first direction, for example. The Lissajous scanning is performed by combining vibration (scanning) in the first direction and vibration (scanning) in the second direction which differ in frequency. A difference between a driving signal frequency in the first direction and a driving signal frequency in the second direction is an integer.

In the optical fiber scanning apparatus 10, the driving section 25 configured to vibrate the optical fiber 12 includes piezoelectric elements (piezoelectric ceramics) 25A to 25D respectively disposed on four side surfaces 20SSA to 20SSD of the ferrule 20 as a prism-shaped rectangular parallelepiped. In other words, the piezoelectric elements 25A and 25B configured to drive the optical fiber 12 in an up-and-down direction (Y-axis direction) are respectively disposed on the facing side surfaces 20SSA and 20SSB, and the piezoelectric elements 25C and 25D configured to drive the optical fiber 12 in a right-and-left direction (X-axis direction) are respectively disposed on the opposing side surfaces 20SSC and 20SSD.

Note that when a reference numeral denotes each of a plurality of components, one alphabet character at the end of the reference numeral is omitted. For example, each of the piezoelectric elements 25A to 25D is referred to as a piezoelectric element 25.

The piezoelectric element (driving section) 25 expands and contracts when an alternating current driving signal (driving voltage) having a predetermined frequency is applied to the piezoelectric element 25 via the signal line 14. Accordingly, when a Y-axis driving signal is applied to the piezoelectric elements 25A and 25B, the free end 12F1 of the optical fiber 12 vibrates in the first direction (Y-axis direction). When an X-axis driving signal is applied to the piezoelectric elements 25C and 25D, the free end 12F1 of the optical fiber 12 vibrates in the second direction (X-axis direction).

When the control unit 5 controls the driving signal generation unit 4, a driving signal for performing two-dimensional scanning in a predetermined pattern is inputted to the driving section 25. In other words, the X-axis driving signal and the Y-axis driving signal which are controlled such that an irradiation position of the spot illumination light to be irradiated onto the object to be observed draws a trajectory corresponding to a predetermined scanning pattern are inputted to the driving section 25.

To perform the two-dimensional scanning in the predetermined pattern, when the vibration in the X-axis direction and the vibration in the Y-axis direction are independently controlled (scanned) at a resonance frequency or a frequency in the vicinity of the resonance frequency in at least one of the axis directions, a driving efficiency is good. However, if the optical fiber 12 has the same resonance frequency FR in both the X-axis direction and the Y-axis direction, even when the scanning is being performed in the X-axis direction, for example, the scanning is also unintentionally performed in the Y-axis direction. Thus, a distortion may occur in a scan trajectory.

The resonance frequency FR of the optical fiber 12 is inversely proportional to a square root of a length (vibration length) L of a vibration section from the fixed end 12F2 to the free end 12F1 in primary resonance. In other words, the smaller the vibration length L is, the higher the resonance frequency FR becomes. In the optical fiber 12, although the vibration length in the X-axis direction and the vibration length in the Y-axis direction are the same, effective vibration lengths differ from each other. Thus, a resonance frequency at the time when the optical fiber 12 vibrates in the X-axis direction and a resonance frequency at the time when the optical fiber 12 vibrates in the Y-axis direction differ from each other.

In other words, in the optical fiber scanning apparatus 10, the optical fiber 12 is fixed with the fixed end 12F2 sandwiched between the pair of first fixing members 30A and 30B composed of solder in the first direction (Y-axis direction) and is fixed with the fixed end 12F2 sandwiched between the pair of second fixing members 30C and 30D composed of nickel in the second direction (X-axis direction).

More specifically, four grooves T20A to T20D each having an opening on a wall surface of the through hole H20 are respectively formed at positions which are rotationally symmetric around the optical axis O on the distal end surface 20SA of the ferrule 20. The groove T20A and the groove T20B are arranged to face each other on opposite sides of the through hole H20. Thus, the grooves T20A and T20B, together with the through hole H20, apparently constitute a continuous single groove. Similarly, the grooves T20C and T20D, together with the through hole H20, constitute a continuous single groove. A long-axis direction of the grooves T20A and T20B is the first direction (Y-axis direction), a long-axis direction of the grooves T20C and T20D is the second direction (X-axis direction), and a depth direction of the grooves 20A to 20D is the optical axis direction (Z-axis direction).

Solder composing the first fixing members 30A and 30B is embedded in the pair of grooves T20A and T20B facing each other, and nickel composing the second fixing members 30C and 30D is embedded in the pair of grooves T20C and T20D facing each other.

Note that the groove T20 may be embedded with the fixing member 30 only at least in the vicinity of the optical fiber 12 (the through hole H20), and the groove T20 needs not be filled with the fixing member 30 over its entire length. For example, the groove T20 may not be filled with the fixing member 30 in the vicinity of the side surface 20SS of the ferrule 20.

Solder composing the first fixing members 30A and 30B has a Young's modulus Y1 of 42 GPa, and nickel composing the second fixing members 30C and 30D has a Young's modulus Y2 of 207 GP.

Accordingly, a fixed state of the fixed end 12F2 differs, and the effective vibration length in the X-axis direction and the effective vibration length in the Y-axis direction differ from each other. The effective vibration length in the first direction in which the fixed end 12F2 is fixed by the first fixing members 30A and 30B is larger than the effective vibration length in the second direction in which the fixed end 12F2 is fixed by the second fixing members 30C and 30D having a larger Young's modulus.

Accordingly, a resonance frequency FR1 in the first direction of the optical fiber 12 is 7824 Hz, and a resonance frequency FR2 in the second direction of the optical fiber 12 is 7890 Hz (ternary resonance in both the first direction and the second direction). In other words, the resonance frequency FR1 in the first direction in which the fixed end 12F2 is fixed by the first fixing members 30A and 30B is lower than the resonance frequency FR2 in the second direction in which the fixed end 12F2 is fixed by the second fixing members 30C and 30D having a larger Young's modulus than the Young's modulus of the first fixing members 30A and 30B. A difference dFR between the resonance frequency FR1 and the resonance frequency FR2 is 66 Hz, and a ratio of the resonance frequency FR1 to the resonance frequency FR2 is 0.84%.

In the optical fiber scanning apparatus 10, the resonance frequency FR1 and the resonance frequency FR2 differ from each other. In the Lissajous scanning, an X-axis driving signal and a Y-axis driving signal can be respectively alternating current signals having substantially the same frequencies as the resonance frequencies in the first direction and the second direction. Accordingly, the optical fiber scanning apparatus 10 can perform stable scanning without a distortion occurring in the scan trajectory.

Note that the through hole H20 is arranged at a center of the ferrule 20, i.e., an equal distance from the four side surfaces 20SSA to 20SSD. The optical fiber 12 matches a central axis of the driving section 25 by being only inserted into the through hole H20.

The optical fiber scanning apparatus 10 is easily manufactured because the optical fiber 12 needs not be processed. In the optical fiber 12, the fixed end 12F2 is fixed by the first fixing members 30A and 30B and the second fixing members 30C and 30D. Thus, the vibration length is the same in the X-axis direction and the Y-axis direction. Accordingly, control to causes the free end 12F2 of the optical fiber 12 to scan two-dimensionally by the control unit 5 is easy. The endoscope 9 including the optical fiber scanning apparatus 10 is easily controlled and manufactured because stable scanning can be performed.

In other words, although the optical fiber 12 has the same configuration in the directions (X-axis direction/Y-axis direction) perpendicular to the optical axis in the optical fiber scanning apparatus 10, the Young's modulus Y1 of the first fixing members 30A and 30B which sandwich and fix the optical fiber 12 in the distal end portion of the ferrule 20 is smaller than the Young's modulus Y2 of the second fixing members 30C and 30D. Note that the Young's modulus Y1 may be larger than the Young's modulus Y2. In other words, the first fixing members 30A and 30B and the second fixing members 30C and 30D may be respectively composed of materials having different Young's moduli. Accordingly, in the optical fiber scanning apparatus 10, the resonance frequency FR1 at the time when the optical fiber 12 vibrates in the first direction (Y-axis direction) and the resonance frequency FR2 at the time when the optical fiber 12 vibrates in the second direction (X-axis direction) differ from each other.

Although the difference dFR between the resonance frequencies required to perform stable scanning irradiation differs depending on a specification of the optical fiber scanning apparatus 10, the resonance frequencies preferably differ by 0.2% or more, and particularly preferably differ by 0.5% or more, for example.

In the Lissajous scanning, an upper limit of the frequency of the Y-axis driving signal is less than ((Y-axis resonance frequency FR1)+(0.5 dFR)), and is preferably less than ((Y-axis resonance frequency FR1)+(0.25 dFR)). A lower limit of the frequency of the Y-axis driving signal is preferably (0.9×(Y-axis resonance frequency FR1)) or more to efficiently drive the optical fiber 12.

Similarly, a lower limit of the frequency of the X-axis driving signal is more than ((X-axis resonance frequency FR2)−(0.5 dFR)), and is preferably more than ((Y-axis resonance frequency FR2)−(0.25 dFR)). An upper limit of the frequency of the X-axis driving signal is preferably (1.1×(X-axis resonance frequency FR2)) or less to efficiently drive the optical fiber 12.

If a scanning method is the Lissajous scanning, the difference dFR between the resonance frequency FR1 in the first direction and the resonance frequency FR2 in the second direction of the optical fiber 12 is preferably kN (Hz) (N and k are natural numbers) in an endoscope which shoots a movie with a frame rate of N (fps) with the reflected light from the object to be observed illuminated with the illumination light.

For example, one still image is shot in $\frac{1}{30}$ seconds in a movie with a frame rate of 30 fps. In other words, both one cycle of scanning in the first direction and one cycle of scanning in the second direction are $\frac{1}{30}$ seconds. If the difference dFR between the resonance frequencies is a multiple of the frame rate N, e.g., 30 Hz, 60 Hz, or 90 Hz, a start time and an end time of the one cycle of the scanning in the first direction and a start time and an end time of an N-th cycle of the scanning in the second direction match each other.

Note that the difference dFR between the resonance frequency FR1 and the resonance frequency FR2 is adjusted by a difference dY between the Young's modulus Y1 of the first fixing members 30A and 30B and the Young's modulus Y2 of the second fixing members 30C and 30D. In other words, the larger the difference between the Young's moduli is, the larger the difference dFR between the resonance frequencies becomes.

In the optical fiber scanning apparatus 10, the first fixing members 30A and 30B and the second fixing members 30C and 30D are composed of metal. However, resin such as epoxy resin (a Young's modulus: 3.5 GPa) or silicone resin (a Young's modulus: 4 MPa) can also be used as a material for the fixing members.

In other words, at least one of the first fixing members 30A and 30B, and the second fixing members 30C and 30D may be composed of resin. Needless to say, at least one of the first fixing members 30A and 30B, and the second fixing members 30C and 30D may be composed of metal.

As the material for the fixing members, the first fixing members 30A and 30B are preferably composed of metal having a Young's modulus an absolute value of which is large, such as nickel, solder, gold (a Young's modulus: 80 GPa), or copper (a Young's modulus: 130 GPa) and the second fixing members 30C and 30D are preferably composed of resin having a Young's modulus an absolute value of which is small because a difference between the Young's moduli is easily increased. Needless to say, the second fixing members 30C and 30D may be composed of resin, and the second fixing members 30C and 30D may be composed of metal.

Modifications to First Embodiment

Respective optical fiber scanning apparatuses according to modifications to the first embodiment are similar to and have the same effect as the effect of the optical fiber scanning apparatus 10. Thus, components having the same functions are assigned the same reference numerals, and description of the components is omitted.

Modification 1 to First Embodiment

Figure 6:
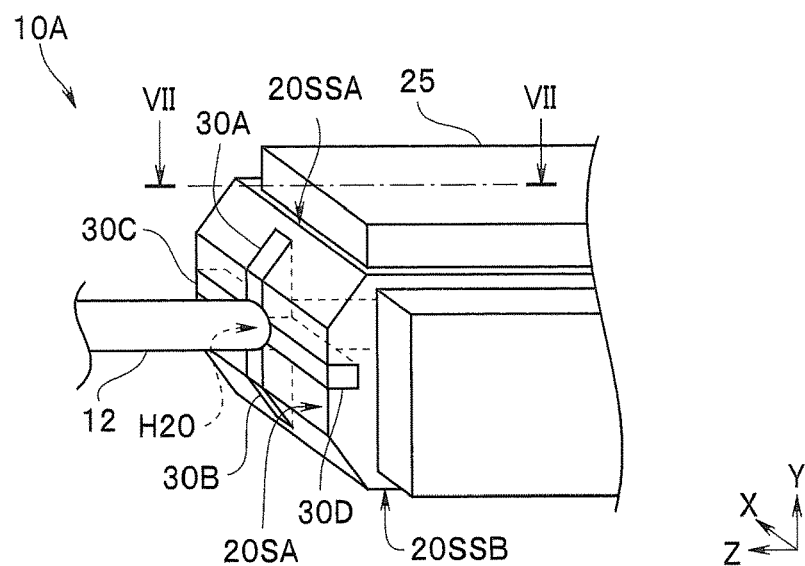
FIG. 6 is a perspective view of a principal part of an optical fiber scanning apparatus according to a modification 1 to the first embodiment.
Figure 7:
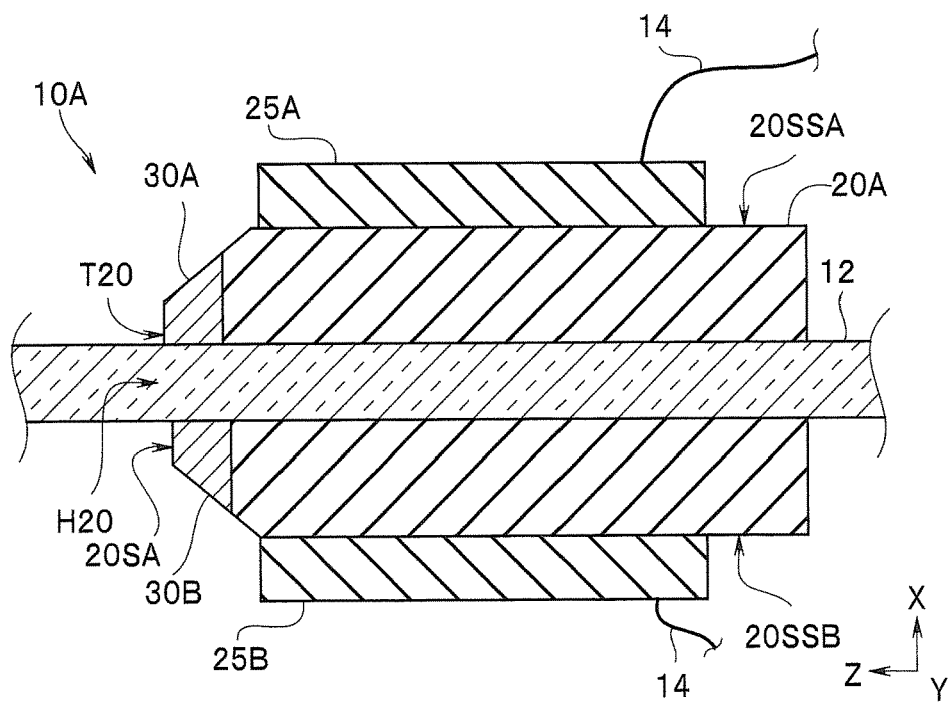
FIG. 7 is a cross-sectional view along a line VII-VII illustrated in FIG. 6 of the principal part of the optical fiber scanning apparatus according to the modification 1 to the first embodiment.

In an optical fiber scanning apparatus 10A according to a modification 1 illustrated in FIGS. 6 and 7, corner portions respectively formed between a distal end surface 20SA and side surfaces 20SSA and 20SSB of a ferrule 20A are chamfered.

The optical fiber scanning apparatus 10A uses the same fixing members 30A to 30D as the fixing members used by the optical fiber scanning apparatus 10. In other words, respective corner portions, between the distal end surface 20SA and the side surfaces 20SSA and 20SSB, of grooves T20A and T20B embedded with fixing members 30A and 30B each having a small Young's modulus are chamfered (notched).

In the optical fiber scanning apparatus 10A, a difference dFR between resonance frequencies is larger than the difference dFR between the reference frequencies in the optical fiber scanning apparatus 10. This is presumed to be because an influence of the fixing members 30A and 30B respectively embedded in the grooves T20A and T20B the corner portions of which are chamfered on vibration of the optical fiber 12 is larger than an influence of the fixing members 30C and 30D respectively embedded in grooves T20C and T20D corner portions of which are not chamfered.

The optical fiber scanning apparatus 10A can perform more stable scanning because the difference dFR between the resonance frequencies is larger than the difference dFR between the resonance frequencies in the optical fiber scanning apparatus 10.

Note that a width W, a depth D, and a length S of the groove T20 are designed depending on a specification. For example, if an outer diameter of the optical fiber 12 is 125 μm, and a length (vibration length) L from a fixed end 12F2 to a free end 12F1 is 10 mm, the width W is 80 μm to 125 μm, and the depth D is 150 μm to 300 μm.

Modification 2 to First Embodiment

A width W of a groove T20 in a shape of the groove T20 exerts a largest influence on a resonance frequency FR.

Figure 8:
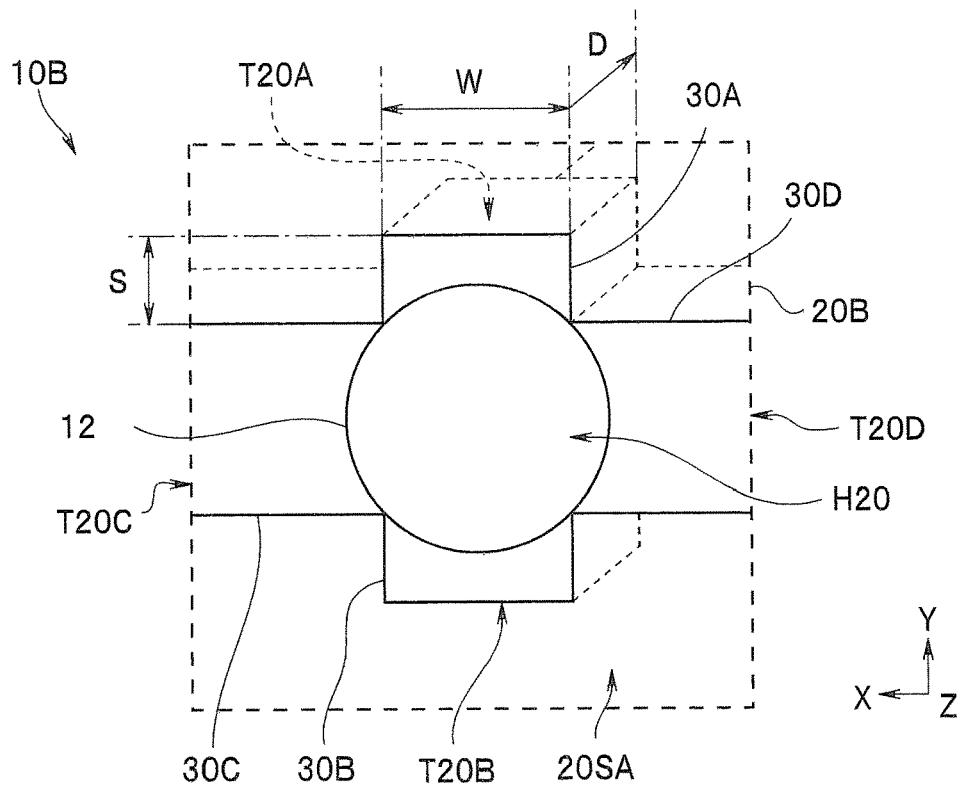
FIG. 8 is a front view of a ferrule in a principal part of an optical fiber scanning apparatus according to a modification 2 to the first embodiment.

In a ferrule 20B in an optical fiber scanning apparatus 10B according to a modification 2 illustrated in FIG. 8, the width W of the groove T20 is large, and an entire periphery of an optical fiber 12 is covered with first fixing members 30A and 30B and second fixing members 30C and 30D which are embedded in the groove T20. In the optical fiber scanning apparatus 10B, the width W of the groove T20 is large. Thus, a resonance frequency FR can be more efficiently changed.

Further, in the ferrule 20B, grooves T20A and T20B in a Y-axis direction each have a small length S. In other words, the groove T20 may not reach a side surface 20SS of the ferrule. However, two grooves T20C and T20D which reach the side surface 20SS of the ferrule can be simultaneously formed using a dicing saw or the like. Accordingly, the groove T20 extending to the side surface 20SS of the ferrule, that is, the groove T20 having an opening on the side surface 20SS of the ferrule is preferable.

Modification 3 to First Embodiment

Figure 9:
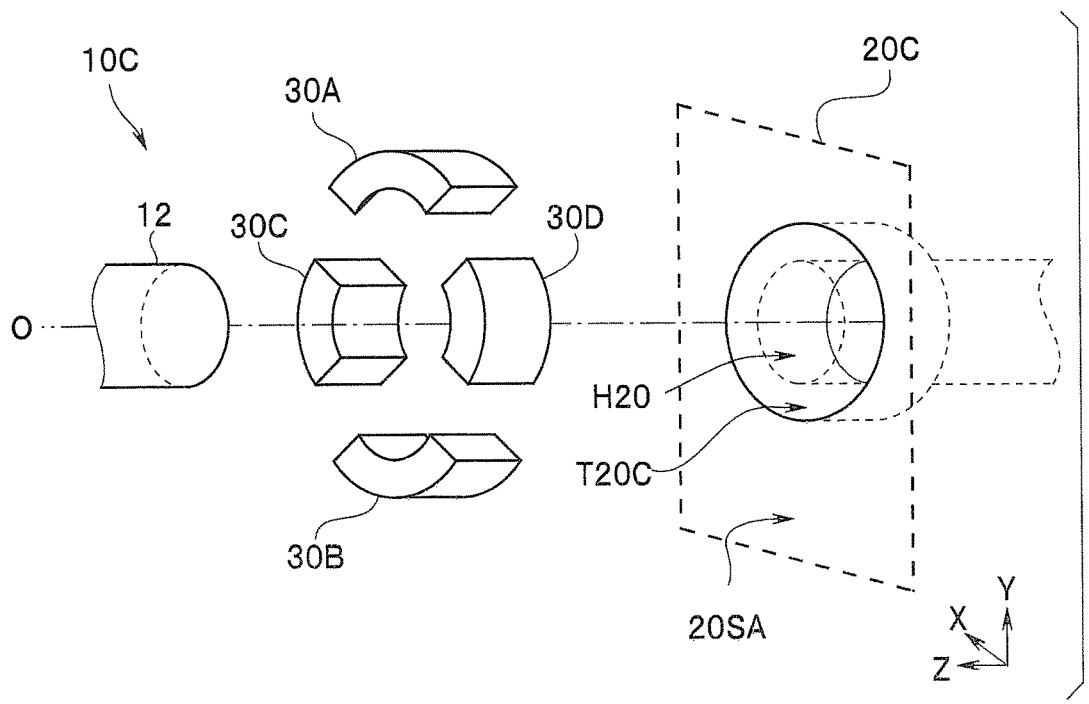
FIG. 9 is an exploded view of a principal part of an optical fiber scanning apparatus according to a modification 3 to the first embodiment.

In an optical fiber scanning apparatus 10C according to a modification 3 illustrated in FIG. 9, a groove T20C is a donut-shaped recess portion formed over an entire outer periphery of a through hole H20. In other words, a diameter of the through hole H20 on a distal end surface 20SA of a ferrule 20C is apparently large.

First fixing members 30A and 30B and second fixing members 30C and 30D are each designed to match a shape of the groove T20C and an outer diameter of an optical fiber 12, and are combined to be embedded in the groove T20C, to fix the optical fiber 12.

Note that although an outer periphery of the groove T20C in the optical fiber scanning apparatus 10C is circular, the outer periphery may be rectangular or polygonal.

Modification 4 to First Embodiment

Figure 10:
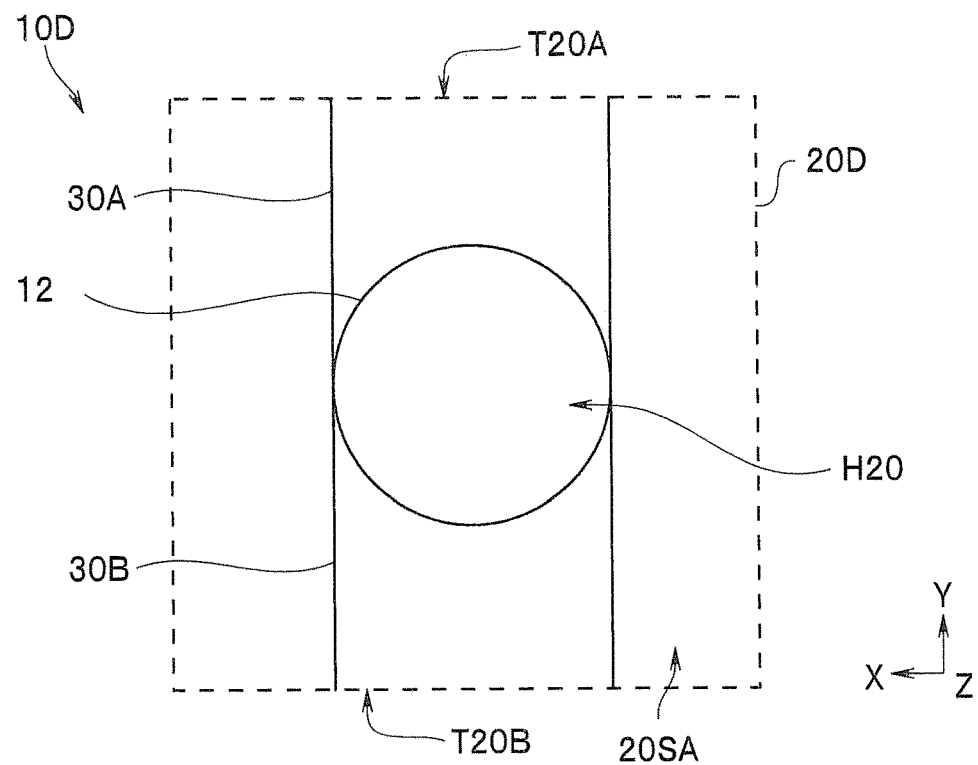
FIG. 10 is a front view of a principal part of an optical fiber scanning apparatus according to a modification 4 to the first embodiment.

In an optical fiber scanning apparatus 10D according to a modification 4 illustrated in FIG. 10, an outer periphery of an optical fiber 12 is fixed by first fixing members 30A and 30B each composed of silicone resin (a Young's modulus: 4 MPa) embedded in a pair of grooves T20A and T20B facing each other in a first direction (Y-axis direction). The outer periphery of the optical fiber 12 is fixed by a wall surface of a through hole H20 in a ferrule 20D composed of nickel (a Young's modulus: 207 GPa) in a second direction (X-axis direction). Note that although a width of the pair of grooves T20A and T20B may be smaller than a diameter of the through hole H20, the width W is preferably substantially the same as the diameter.

The optical fiber scanning apparatus 10D according to the modification 4 has the same effect as the effect of the optical fiber scanning apparatus 10 because a first fixing member which fixes the optical fiber 12 in the first direction and a second fixing member which fixes the optical fiber 12 in the second direction differ in Young's modulus. The width W of the grooves can be made larger. Thus, a resonance frequency FR can be more effectively changed.

In the optical fiber scanning apparatus according to the embodiment, at least one of a first fixing member and a second fixing member may be formed on a distal end surface and embedded in a groove having an opening on a wall surface of a through hole.

Second Embodiment

An optical fiber scanning apparatus 10E according to a second embodiment is similar to and has the same effect as the effect of the optical fiber scanning apparatus 10. Thus, components having the same functions are assigned the same reference numerals, and description of the components is omitted.

Figure 11:
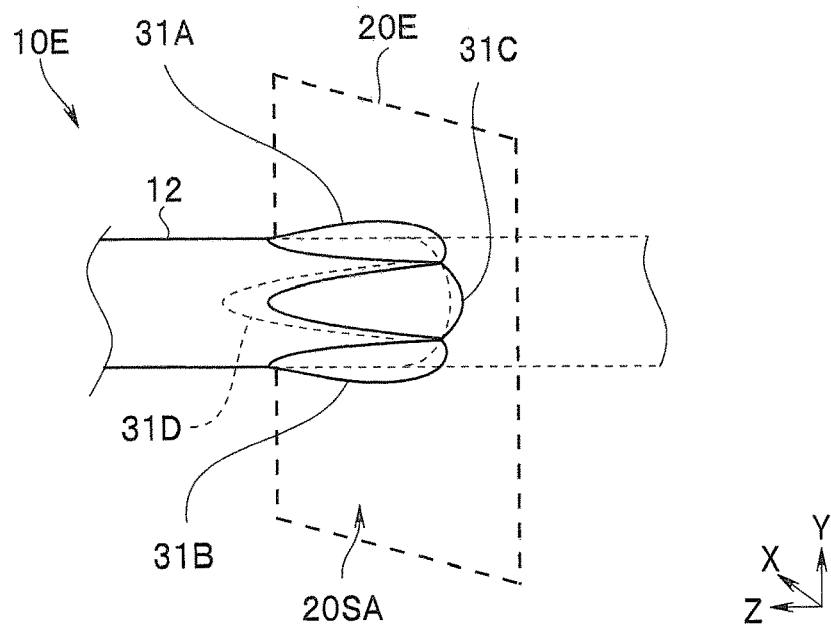
FIG. 11 is a perspective view of a principal part of an optical fiber scanning apparatus according to a second embodiment.

As illustrated in FIG. 11, in the optical fiber scanning apparatus 10E, an optical fiber 12 is fixed by a fixing member 31 disposed on a distal end surface 20SA of a ferrule 20E.

An outer periphery of the optical fiber 12 is fixed by first fixing members 31A and 31B composed of epoxy resin in a first direction (Y-axis direction), and is fixed by second fixing members 31C and 31D composed of solder in a second direction (X-axis direction). Note that an outer peripheral surface of the optical fiber 12 on which the second fixing members 31C and 31D are disposed is coated with gold which can be solder-bonded.

The optical fiber scanning apparatus 10E is easily manufactured because a groove to be embedded with a fixing member needs not be formed in the ferrule 20.

Note that in the foregoing description, the optical fiber scanning apparatus 10 using the piezoelectric driving method in which the driving section includes the piezoelectric elements 25, for example, has been described. However, the optical fiber scanning apparatus according to the embodiment may use an electromagnetic driving method in which the driving section includes a magnet. In the electromagnetic driving method, an alternating current magnetic field is applied from outside to an optical fiber to which a magnetic body (magnet) is attached. In the optical fiber scanning apparatus using the electromagnetic driving method, a holding section (ferrule) may be not a rectangular parallelepiped but a circular column or a polygonal column having a polygon with five or more sides and angles as its base.

Although the Lissajous scanning has been mainly described as the scanning method, when resonance frequencies in an X-axis direction and a Y-axis direction are also made to differ in the spiral scanning or the raster scanning, an unexpected trajectory does not easily occur in respective vibrations in the axis directions so that a trajectory having little distortion can be obtained.

In the above-described optical fiber scanning apparatus 10, for example, the first fixing member and the second fixing member are the same in shape, particularly the same in a shape of an abutment surface abutting on an optical fiber, and are the same in area. However, the first fixing member and the second fixing member may respectively have different shapes.

Note that it goes without saying that an endoscope including any one of the optical fiber scanning apparatuses 10A to 10D according to the modifications to the first embodiment or the optical fiber scanning apparatus 10E according to the second embodiment has an effect of the endoscope 9 according to the first embodiment, and further has an effect of the optical fiber scanning apparatus included in the endoscope.

The present invention is not limited to each of the above-described embodiments and modifications, but various changes, combinations, and applications are possible without departing from the scope and spirit of the invention.

What is claimed is:

1. An optical fiber scanning apparatus comprising:
   an optical fiber configured to emit illumination light from a free end of the optical fiber, the free end being configured to move according to a vibration of the optical fiber;
   a drive apparatus configured to vibrate the free end of the optical fiber in a first direction and in a second direction perpendicular to the first direction;
   a ferrule comprising:
      a through hole through which the optical fiber is inserted, the through hole being extended in an optical axis direction;
      a pair of first grooves formed on a distal end surface of the ferrule in the first direction, each of the pair of first grooves including an opening on a wall surface of the through hole; and
      a pair of second grooves formed on the distal end surface of the ferrule in the second direction, each of the pair of second grooves including the opening on a wall surface of the through hole;
   a pair of first fixing members respectively embedded in the pair of first grooves to fix the optical fiber with respect to the first direction; and
   a pair of second fixing members respectively embedded in the pair of second grooves to fix the optical fiber with respect to the second direction.

2. The optical fiber scanning apparatus according to claim 1, wherein the pair of first fixing members and the pair of second fixing members are composed of different materials, respectively.

3. The optical fiber scanning apparatus according to claim 1, wherein:
   the pair of first fixing members are composed of a first material having a first Young's modulus,
   the pair of second fixing members are composed of a second material having a second Young's modulus, and
   the first Young's modulus is smaller than the second Young's modulus.

4. The optical fiber scanning apparatus according to claim 1, wherein at least one of the pair of first fixing members and at least one of the pair of second fixing members is composed of resin.

5. The optical fiber scanning apparatus according to claim 1, wherein at least one of the pair of first fixing members and at least one of the pair of second fixing members is composed of metal.

6. The optical fiber scanning apparatus according to claim 1, wherein among corner portions respectively formed between the distal end surface and side surfaces of the ferrule, the corner portions in a direction in which the pair of first fixing members is disposed are chamfered.

* * * * *